[19] United States Patent

[11] 4,210,611

Crosby et al.

[45] Jul. 1, 1980

[54] HALOGENATED HYDROCARBONS, USEFUL AS INSECTICIDE INTERMEDIATES, AND METHODS FOR THEIR PREPARATION

[75] Inventors: John Crosby; Bernard W. H. Terry, both of Manchester, England

[73] Assignee: Imperial Chemical Industries Limited, London, England

[21] Appl. No.: 40,455

[22] Filed: May 18, 1979

[30] Foreign Application Priority Data

May 25, 1978 [GB] United Kingdom ............... 22429/78

[51] Int. Cl.$^2$ .............................................. C07C 17/28
[52] U.S. Cl. ................................. 260/653.5; 260/653.3
[58] Field of Search ................... 260/653, 653.5, 653.3

[56] References Cited

U.S. PATENT DOCUMENTS 3,925,491  12/1975  Riess et al. ...................... 260/653.3

Primary Examiner—C. Davis
Attorney, Agent, or Firm—Cushman, Darby & Cushman

[57] ABSTRACT

Halogenated hydrocarbons of formula:

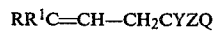

and

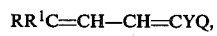

and mixtures thereof, wherein Y is F, Cl or Br, R is hydrogen or a lower alkyl group, $R^1$ is a lower alkyl group, Z is Y or Q and Q is $W(CF_2)_m-$ in which W is hydrogen, F or Cl and m is 1 or 2, and a process for their preparation which comprises heating in a polar aprotic solvent, preferably in the presence of an alkali metal halide, a halogenated hydrocarbon of formula $RR^1C-CHX-CH_2CYZQ$ wherein $R,R^1,Y,Z$ and Q have the previously defined meanings and X is Cl, Br or I, provided that X is always Br or I when at least one of Y and Z is Br.

5 Claims, No Drawings

HALOGENATED HYDROCARBONS, USEFUL AS INSECTICIDE INTERMEDIATES, AND METHODS FOR THEIR PREPARATION

This invention relates to halogenated hydrocarbons, useful as insecticide intermediates, and to methods for their preparation.

According to the present invention there are provided a helogenated hydrocarbon having the general formula:

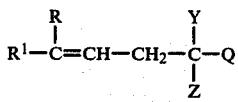

and a halogenated hydrocarbon having the general formula:

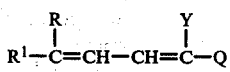

wherein
Y represents a fluorine, chlorine or bromine atom, R represents a hydrogen atom or a lower alkyl group and
$R^1$ represents a lower alkyl group,
Z is Y or Q, and
Q is $W(CF_2)_m$ in which W is hydrogen, fluorine or chlorine and m is 1 or 2.

Preferably the halogen atoms represented by Y and Z are chlorine or bromine atoms, especially chlorine atoms.

By "lower alkyl group" we mean an alkyl group containing from 1 to 6 carbon atoms, preferably a methyl group.

Compositions of matter comprising mixtures of compounds of formula (I) and (II) are also within the scope of the invention.

According to a further feature of the invention there is provided a process for the manufacture of the halogenated hydrocarbons (I) and (II) which comprises heating in a polar aprotic solvent a halogenated hydrocarbon having the general formula:

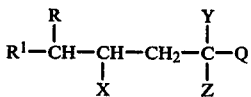

wherein R, $R^1$, Y, Z and Q have the meanings defined above and X represents chlorine, bromine or iodine, provided that X is always bromine or iodine when at least one of Y and Z is bromine.

An example of a compound of formula (III) which may be used in the above process is 5-methyl-2,2,4-trichloro-1,1,1-trifluorohexane.

Examples of polar aprotic solvents which may be used in the process are dimethylacetamide, diethylformamide, hexamethylphosphoramide, dimethylsulphoxide and especially dimethylformamide. The rate of reaction may be increased by carrying out the reaction in the presence of an alkali metal halide, and this is a preferred feature of the invention.

Examples of the alkali metal halides which may be used are the fluorides, chlorides, bromides or iodides of lithium, sodium and potassium. A preferred alkali metal halide is lithium chloride.

The amount of polar aprotic solvent which is used may be from 2 to 200 moles, preferably 4 to 20 moles, per mole of the starting material of formula (III). The amount of alkali metal halide which is used may be from 0.01 to 10.0 moles, preferably 0.10 to 2.0 moles, per mole of the compound of formula (III).

The reaction may be carried out at a temperature from 50° to 300° C., conveniently from 130° to 180° C. and may require a reaction time of several hours to several days. Depending upon the particular solvent and compound of formula (III) used it may be necessary to carry out the reaction at superatmospheric pressure to achieve the desired temperature. The compound of formula (I) occurs as an intermediate in the formation of the compound of formula (II), and if the reaction is allowed to proceed to completion, the compound of formula (II) will be the only product of the reaction. By stopping the reaction at an intermediate stage, a mixture of the compounds of formula (I) and (II) is obtained. The two components can be separated, for example, by preparative gas-liquid chromatography. The course of the reaction can be followed by gas-liquid chromatographic (GLC) analysis.

The compounds of formula (III) which are the starting materials for the preparation of compounds (I) and (II) according to the present invention may be prepared by suitable classical processes of organic chemistry, for example, by reacting a 3,3-dialkylprop-1-ene with a trihalogenated trifluoroethane in the presence of a suitable catalyst, as more fully described in our copending United Kingdom patent application of even date.

Dienes of formula (II) are useful as intermediates in the preparation of insecticides based on certain cyclopropane carboxylic acids; they can be converted by various methods into the carboxylic acid or ester of the formula:

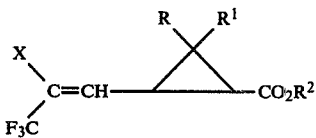

where $R^2$ is H or lower alkyl. These latter compounds may be further converted by esterification or transesterification into the corresponding esters with, for example, m-phenoxybenzyl alcohol or its α-cyano or α-ethinyl derivatives, which esters, when $R=R^1=CH_3$, are very valuable insecticides. These reactions and variants of them are more fully described in certain of our earlier copending United Kingdom patent applications.

The invention is illustrated but not limited by the following Examples in which parts and percentages are by weight.

EXAMPLE 1

5-Methyl-2,2,4-trichloro-1,1,1-trifluorohexane (257.5 parts) and lithium chloride (10 parts) dissolved in dimethylformamide (584.8 parts) are charged to a reaction vessel equipped with a condenser and an internal thermometer and heated to 130° C. The progress of the reaction is monitored by GLC analysis (1.5 m column; 10% E 301 on celite, at 77° C.) which reveals the presence of two components in addition to the starting material. When analysis indicated that all the starting material has reacted and that only one reaction product is present (after 3-4 days), the reaction mixture is cooled and drowned into water (10,000 parts) to precipitate most of the crude product. The remaining product is recovered by extraction of the aqueous solution with dichloromethane, followed by removal of the dichloromethane from the extract by distillation.

The combined crude product is freed from residual dimethylformamide by washing with water and is then dried and distilled to give 2-chloro-5-methyl-1,1,1-trifluorohexa-2,4-diene (145.9 parts; 79%), b.p. 91°-94° C., 140 mm Hg pressure; $'H_{nmr}(CDCl_3)$: $\tau$8.16 (d, 6H), 3.87 (broadened d, H), 3.15 and 2.95 (pair of doublets, H) (in the ratio approximately 1:9); infra red (NaCl) 1645 cm$^{-1}$ (C=C); mass spectrum: m/e 184;

EXAMPLE 2

5-Methyl-2,2,4-trichloro-1,1,1-trifluorohexane (120 parts) and lithium chloride (7.0 parts) dissolved in dimethylformamide (570 parts) are heated together as described in Example 1, except that the reaction is stopped after 9 hours. At this stage the reaction mixture contains approximately equal parts of two reaction products together with some unreacted starting material. The reaction mixture is worked up as described in Example 1 to give a product free from dimethylformamide, and is separated into its components by preparative GLC (column length 2.1 m; diameter 95 mm; 15% E301 on celite, at 85° C.). One component reaction product of the mixture is 2-chloro-5-methyl-1,1,1-trifluorohexa-2,4-diene, already identified in Example 1. The other component reaction product is 2,2-dichloro-5-methyl-1,1,1-trifluorohex-4-ene, $'H_{nmr}(CDCl_3)$: $\tau$8.25 (d, 6H), 7.03 (d, 2H), 4.66 (t, H); infra red (NaCl) 1675 cm$^{-1}$ (C=C); mass spectrum: m/e 220.

We claim:

1. A halogenated hydrocabon having the general formula:

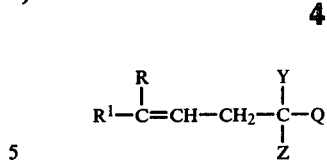

and a halogenated hydrocarbon having the general formula:

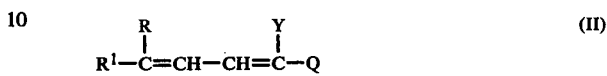

and mixtures thereof, wherein
Y represents fluorine, chlorine or bromine,
R represents hydrogen or a lower alkyl group,
R$^1$ represents a lower alkyl group,
Z is Y or Q and
Q is W(CF$_2$)$_m$—in which W is hydrogen, fluorine or chlorine and
m is 1 or 2.

2. Halogenated hydrocarbons as claimed in claim 1 wherein Y and Z are chlorine or bromine.

3. 2-Chloro-5-methyl-1,1,1-trifluorohexa-2,4-diene.

4. 2,2-Dichloro-5-methyl-1,1,1-trifluorohex-4-ene.

5. A process for the preparation of the halogenated hydrocarbons claimed in claim 1 which comprises heating in a polar aprotic solvent a halogenated hydrocarbon having the general formula:

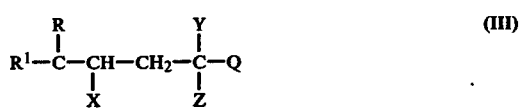

wherein R, R$^1$, Y, Z and Q have the meanings defined in claim 1 and X represents chlorine, bromine or iodine; provided that X is always bromine or iodine when at least one of Y and Z is bromine.

* * * * *